United States Patent

Sargent et al.

[11] Patent Number: 5,945,831
[45] Date of Patent: Aug. 31, 1999

[54] VOLUME CHARGE DENSITY MEASURING SYSTEM

[76] Inventors: John S. Sargent, 1712 Manchester Pl., Escondido, Calif. 92027; Frank T. Sargent, 9433 Brandy Cir., Fort Myers, Fla. 33919

[21] Appl. No.: 08/872,875

[22] Filed: Jun. 10, 1997

[51] Int. Cl.[6] .................................................. G01R 27/26
[52] U.S. Cl. ........................... 324/686; 324/663; 324/688
[58] Field of Search .................................... 324/663, 667, 324/674, 686, 688

[56] References Cited

U.S. PATENT DOCUMENTS

| | | | |
|---|---|---|---|
| 2,377,275 | 5/1945 | Smith | 73/304 |
| 2,485,579 | 10/1949 | Elliott | 175/183 |
| 2,599,583 | 6/1952 | Robinson et al. | 175/183 |
| 2,709,785 | 5/1955 | Fielden | 324/701 |
| 2,720,624 | 10/1955 | Gunst et al. | 324/668 |
| 2,807,956 | 10/1957 | Doble | 73/73 |

(List continued on next page.)

FOREIGN PATENT DOCUMENTS

| | | |
|---|---|---|
| 1271524 | 7/1990 | Canada . |
| 0 380 751 | 8/1990 | European Pat. Off. . |
| 0 499 841 A1 | 8/1992 | European Pat. Off. . |
| 3822344 A1 | 1/1990 | Germany . |
| 52-69393 | 9/1977 | Japan . |
| 62-76440 | 4/1987 | Japan . |
| 0972378 | 11/1982 | U.S.S.R. . |

*Primary Examiner*—Glenn W. Brown
*Attorney, Agent, or Firm*—Brown, Martin, Haller & McClain, LLP

[57] ABSTRACT

A capacitive sensor includes a tubular outer conductor, a tubular inner conductor coaxial with the outer conductor, and an electrically insulated chamber between the inner and outer conductors. The material sample to be measured is introduced into the chamber. The sensor is shielded against electric fields to maximize measurement accuracy. The shielding completely encloses the chamber during operation and may include a removable cap, a valve, or a screen made of a conductive material. A measurement circuit connected to the sensor includes a reference oscillator that oscillates at a constant frequency and a test oscillator that oscillates at a frequency determined by the sensor capacitance. A circuit displays a value representing the sensor capacitance in response to the frequency difference between the test oscillator frequency and the reference oscillator frequency.

18 Claims, 7 Drawing Sheets

U.S. PATENT DOCUMENTS

| | | | |
|---|---|---|---|
| 3,238,452 | 3/1966 | Schmitt et al. | 324/666 |
| 3,421,077 | 1/1969 | Liu et al. | 324/663 |
| 3,469,157 | 9/1969 | Rhodes | 317/246 |
| 3,559,048 | 1/1971 | Bryant | 324/450 |
| 3,635,082 | 1/1972 | Prellwitz et al. | 73/194 M |
| 3,665,301 | 5/1972 | Maltby | 324/690 |
| 3,753,102 | 8/1973 | Beck | 324/109 |
| 3,757,210 | 9/1973 | Hansen et al. | 324/671 |
| 3,764,899 | 10/1973 | Peterson et al. | 324/671 |
| 4,093,915 | 6/1978 | Briefer | 324/679 |
| 4,251,767 | 2/1981 | Montana | 324/676 |
| 4,296,630 | 10/1981 | Jung et al. | 73/304 C |
| 4,363,244 | 12/1982 | Rabeh et al. | 73/861.08 |
| 4,383,444 | 5/1983 | Beaman et al. | 73/304 C |
| 4,434,657 | 3/1984 | Matsumura et al. | 73/304 C |
| 4,467,646 | 8/1984 | Berryman et al. | 73/304 C |
| 4,558,274 | 12/1985 | Carusillo | 324/607 |
| 4,594,553 | 6/1986 | Varga | 324/454 |
| 4,594,893 | 6/1986 | Lombard et al. | 73/304 C |
| 4,651,087 | 3/1987 | Shirato et al. | 324/71.4 |
| 4,658,207 | 4/1987 | Scribano et al. | 324/664 |
| 4,680,552 | 7/1987 | Shirato et al. | 324/439 |
| 4,751,842 | 6/1988 | Ekrann et al. | 73/61.1 R |
| 4,806,847 | 2/1989 | Atherton et al. | 73/304 C |
| 4,809,129 | 2/1989 | Hansen, III et al. | 361/284 |
| 4,820,990 | 4/1989 | Moore | 324/445 |
| 4,823,204 | 4/1989 | Holland | 358/347 |
| 4,939,519 | 7/1990 | Elbert | 341/167 |
| 4,940,667 | 7/1990 | Goldstein et al. | 436/157 |
| 4,961,147 | 10/1990 | Moore | 324/446 |
| 4,982,606 | 1/1991 | Adamski et al. | 73/304 C |
| 4,994,749 | 2/1991 | Davies et al. | 324/637 |
| 5,001,927 | 3/1991 | Lacava et al. | 73/304 C |
| 5,005,402 | 4/1991 | Pischinger et al. | 324/663 |
| 5,017,879 | 5/1991 | Lucas et al. | 324/663 |
| 5,017,909 | 5/1991 | Goekler | 340/620 |
| 5,031,068 | 7/1991 | Hansen, III et al. | 361/284 |
| 5,045,797 | 9/1991 | Kramer et al. | 324/667 |
| 5,046,843 | 9/1991 | Keren | 356/152 |
| 5,051,921 | 9/1991 | Paglione | 364/509 |
| 5,083,470 | 1/1992 | Davis et al. | 73/864.24 |
| 5,085,078 | 2/1992 | Baux et al. | 73/313 |
| 5,122,922 | 6/1992 | Richeson | 361/284 |
| 5,135,485 | 8/1992 | Cohen et al. | 604/67 |
| 5,151,660 | 9/1992 | Powers et al. | 324/689 |
| 5,214,386 | 5/1993 | Singer et al. | 324/452 |
| 5,278,513 | 1/1994 | Kramer et al. | 324/667 |
| 5,293,893 | 3/1994 | O'Dougherty | 137/113 |
| 5,294,889 | 3/1994 | Heep et al. | 324/678 |
| 5,315,872 | 5/1994 | Moser | 73/304 C |
| 5,361,035 | 11/1994 | Meitzler et al. | 324/663 |
| 5,365,783 | 11/1994 | Zweifel | 73/304 C |
| 5,392,657 | 2/1995 | Feller | 73/861.77 |
| 5,397,995 | 3/1995 | Anderson | 324/684 |
| 5,421,210 | 6/1995 | Kobayashi et al. | 73/861.12 |
| 5,446,444 | 8/1995 | Lease | 340/514 |
| 5,457,990 | 10/1995 | Oswald et al. | 73/290 V |
| 5,461,321 | 10/1995 | Sanders et al. | 324/678 |
| 5,477,727 | 12/1995 | Koga | 73/304 C |
| 5,481,197 | 1/1996 | Sanders et al. | 324/690 |
| 5,495,130 | 2/1996 | Schneider | 307/118 |
| 5,546,005 | 8/1996 | Rauchwerger | 324/688 |
| 5,554,937 | 9/1996 | Sanders et al. | 324/664 |
| 5,566,572 | 10/1996 | Pankow et al. | 73/304 C |
| 5,611,240 | 3/1997 | Yamaguchi | 73/304 C |

VOLUME CHARGE DENSITY MEASURING SYSTEM

BACKGROUND OF THE INVENTION

The present invention relates generally to capacitive measuring systems and, more specifically, to a system having a sensor shielded against the detrimental effects of external electric fields for capacitively measuring the volume charge density of a sample of material.

Capacitive measuring systems have been used to measure dissolved solids and impurities in fluids such as water and oil. A capacitive sensor is a device having two electrically conductive electrodes and a non-conductive body that insulates the fluid from the electrodes. The electrodes are typically tubular in shape and concentric with one another. When a sample is placed in the body, the device defines a capacitance in response to the dielectric constant of the sample. The dielectric constant varies in response to the ion concentration in the sample, which, in turn, is related to the solid impurities. The capacitance may be measured by connecting a suitable oscillator and measuring circuit to the plates. Comparing the measured capacitance to a known capacitance provides information relating to the electrical properties of the sample. For example, the dissolved solids in a sample of water can be determined by comparing the measured value to that which is produced in response to a known pure (e.g., double-distilled) sample of water.

Conventional capacitive sensors of the type described above are of low precision. They cannot, for example, consistently measure ion concentrations in water below a few parts per million. Practitioners in the art have discovered that measurements may vary over a wide range under seemingly identical test conditions. It would be desirable to provide a capacitive measuring system having a high-precision sensor. This and other problems and deficiencies are clearly felt in the art and are solved by the present invention in the manner described below.

SUMMARY OF THE INVENTION

The present invention includes a capacitive sensor and an electronic measurement system. The sensor includes a tubular outer conductor, a tubular inner conductor coaxial with the outer conductor, and an electrically insulated chamber between the inner and outer conductors. The material sample to be measured is placed in the chamber or forced to flow through the chamber. The chamber electrically isolates the sample from the conductors. When the sample is introduced into the chamber, it defines the dielectric of a capacitor. The plates of the capacitor are defined by the inner and outer conductors.

It has been discovered in accordance with the present invention that measurements produced by capacitive sensors known in the art are detrimentally affected by external electric fields, i.e., fields produced by environmental sources external to the sensor, such as fluorescent lights. A conductor exposed to an electric field acts as an antenna and develops a potential. If measurements are taken using such a sensor in, for example, a room having fluorescent lighting, the measurements will be markedly different than if taken in a room not having fluorescent lighting. Even in the absence of fluorescent lighting and other apparent sources of electric fields, the body of the person taking the measurements may emit sufficient electromagnetic radiation to affect the measurements.

In accordance with the discovery that electric fields detrimentally affect capacitive impurity measuring systems, the present invention includes electrostatic shielding that completely encloses the chamber in which the sample is contained during measurement. In an exemplary embodiment, the sensor has one or more openings, and a removable cap made of a conductive material is attachable to the opening. No external electric field can penetrate into the chamber because the cap is in electrical contact with the outer conductor and seals the opening during measurement. In another exemplary embodiment, the sensor has one or more openings, and a valve selectably opens or closes the opening. No external electric field can penetrate into the chamber because the valve, which may be solenoid-operated, has a conductive member that is in electrical contact with the outer conductor and seals the opening during measurement. In yet another exemplary embodiment, the sensor has one or more openings in which a screen made of a conductive material is disposed. An external electric field cannot penetrate into the chamber to any significant extent because the screen is in electrical contact with the outer conductor.

The foregoing, together with other features and advantages of the present invention, will become more apparent when referring to the following specification, claims, and accompanying drawings.

BRIEF DESCRIPTION OF THE DRAWINGS

For a more complete understanding of the present invention, reference is now made to the following detailed description of the embodiments illustrated in the accompanying drawings, wherein.

DESCRIPTION OF PREFERRED EMBODIMENTS

As illustrated in FIGS. 1–4, a capacitive sensor 10 includes an elongated, generally tubular inner conductor 12 and an elongated, generally tubular outer conductor 14 that are coaxially or concentrically mounted with respect to one another. Conductors 12 and 14 are radially spaced from one another, thereby defining an elongated annular chamber 16. Outer conductor 14 includes two conductive endpieces 18 and 20, one threadably attached to each end of sensor 10. O-rings 21 and 23 seal endpieces 18 and 20, respectively, against leakage. Endpieces 18 and 20 have sensor inlet and outlet openings 22 and 24, respectively. As more fully described below, sensor 10 may be used to measure the volume charge density of a fluid, i.e., a liquid or gas in chamber 16, which may flow into sensor inlet opening 22 and out of sensor outlet opening 24.

Two body portions 26 and 28 made of a non-conductive material are disposed at opposite ends of sensor 10. Body portion 26 is fit within one end of outer conductor 14, and body portion 28 is fit within the other end of outer conductor 14. One end of inner conductor 12 is captured within an annular groove in body portion 26, and the other end is captured within an annular groove in body portion 28. Body portion 26 has an annular glue tang 30 that snaps into engagement with a corresponding annular groove 32 of body portion 28. This manner of attaching body portion 26 to body portion 28 facilitates economical assembly of the device.

Figure 3:
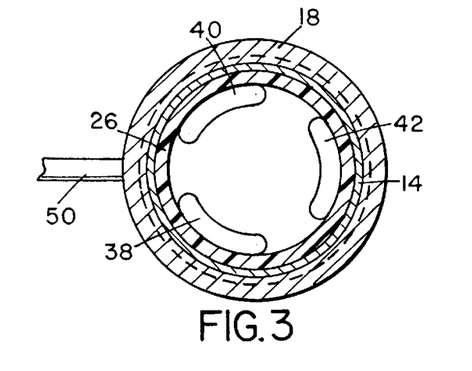
FIG. 3 is a sectional view taken on line 3—3 of FIG. 1.
Figure 4:
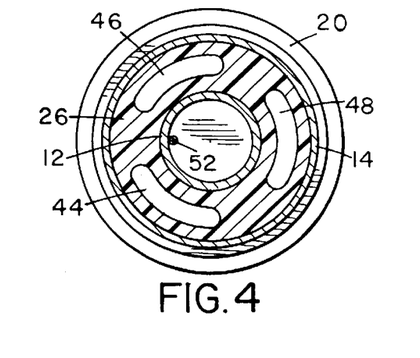
FIG. 4 is a sectional view taken on line 4—4 of FIG. 1.

Body portion 26 has three elongated arcuate fluid channels 38, 40 and 42 disposed at even spacings. Similarly, body portion 28 has three elongated arcuate fluid channels 44, 46 and 48 disposed at even spacings.

Figure 1:
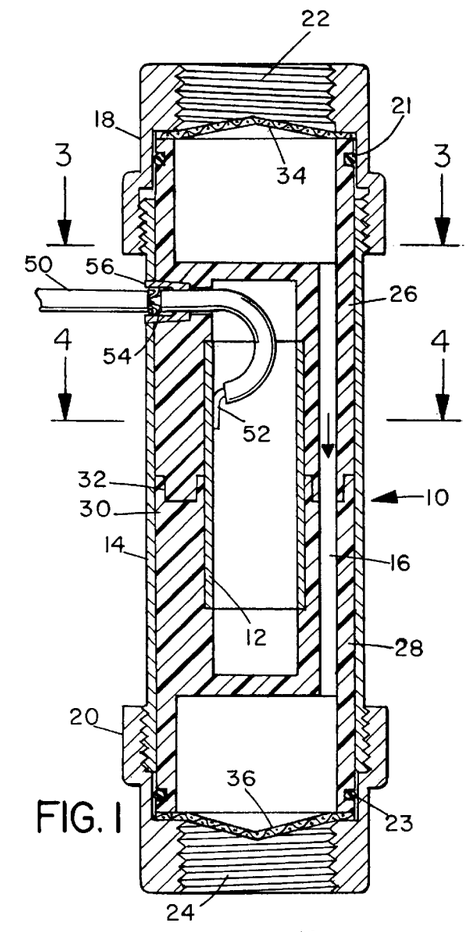
FIG. 1 is a sectional view of a sensor of a type suitable for flow-through operation.

In operation, fluid is introduced into sensor inlet opening 22 in endpiece 18. The fluid enters chamber 16 through fluid channels 38, 40 and 42. The flow exits chamber 16 through fluid channels 44, 46 and 48. Sensor outlet opening 24 in endpiece 20 receives the fluid flow.

Although body portions 26 and 28 insulate the fluid in chamber 16 from electrical contact with inner and outer conductors 12 and 14, in other embodiments the inner and outer conductors may be coated with a suitable dielectric material to insulate them from the fluid. In still other embodiments (not shown), the inner and outer conductors may be coatings of conductive material deposited on concentric tubes made of glass or other insulating material. Although many such embodiments and variations will occur to those skilled in the art in view of these teachings, the common concept among them is that a fluid introduced into a chamber between two conductors and electrically insulated from the conductors by an insulating or dielectric material defines a capacitance.

In other embodiments (not shown), additional chambers may be included concentrically with one another to increase the capacitance of the sensor. In other words, although in the illustrated embodiment the combination of inner and outer conductors 12 and 14 and body portions 26 and 28 define a single chamber 16 electrically illustrated from conductors 12 and 14, in other embodiments additional insulators and conductors arranged in a concentric manner may define additional such chambers.

A coaxial cable 50 electrically connects sensor 10 to the circuitry described below. One end of cable 50 is stripped to expose or bare the center conductor 52. Center conductor 52 is soldered to the inside surface of inner conductor 12. The shield 54 of cable 50 is bared where cable 50 enters outer conductor 14. Nevertheless, cable 50 has shield 54 all along its length between sensor 10 and the associated electronic circuit. A collet 56 secures cable 50 to outer conductor 14 and also makes an electrical connection between outer conductor 14 and shield 54. Cable 50 is preferably not bared between collet 56 and the point at which center conductor 52 is soldered to inner conductor 12 to maximize signal shielding inside sensor 10.

In other embodiments (not shown), some or all of the circuitry described below may be disposed inside the sensor. For example, in certain sensors the capacitance may be so low that the parasitic capacitance of the coaxial cable may affect the sensitivity of the system. Therefore, it may be desirable to dispose at least some of the electronic circuit components inside the sensor rather than externally to it. In certain such embodiments, all of the circuitry may be disposed inside the sensor, and the sensor may include an integral display for indicating the capacitance.

It is important that outer conductor 14, its endpieces 18 and 20, and even collet 56 all be made of a suitable conductive material such as metal and conductively coupled to one another and grounded to promote complete shielding of chamber 16 against external electric fields. As a result of this shielding, the only way for any external electric field to enter would be via openings 22 and 24.

An additional feature that shields against intrusion of external electric fields in certain embodiments comprises screens 34 and 36 disposed in endpieces 18 and 20, respectively. Screens 34 and 36 are made of a conductive material such as woven metal wire that shields against entry of external electric fields during operation. Screens 34 and 36 are preferably conical and have a weave that is sufficiently close to block electric fields to the extent desired, yet sufficiently coarse to permit the desired flow rate through sensor 10.

Figure 2:
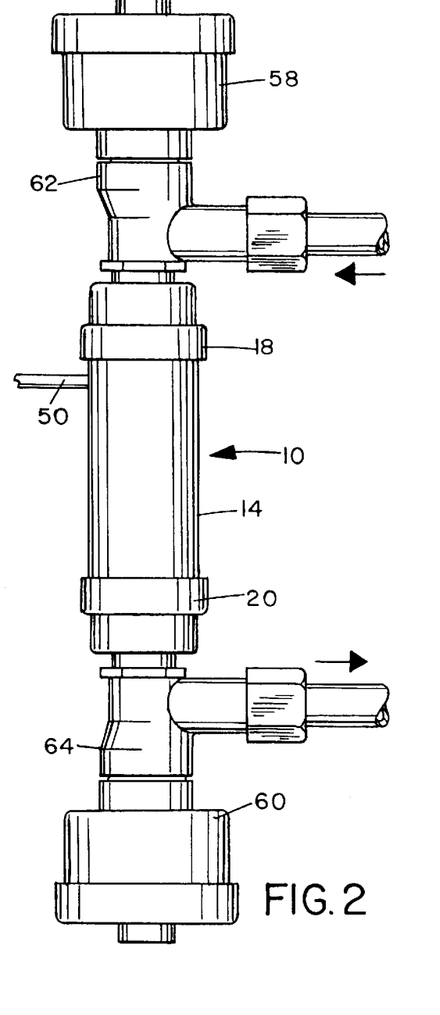
FIG. 2 is a side elevational view of the sensor of FIG. 1 and a solenoid-operated valve connected to the opening at each end of the sensor.
Figure 5:
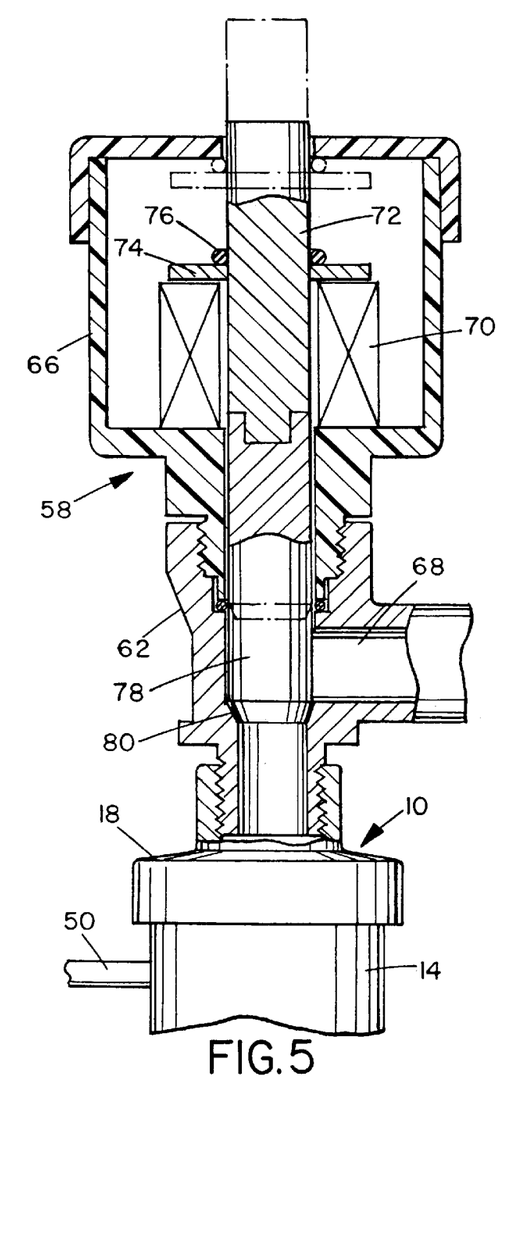
FIG. 5 is an enlargement of one end of the structure illustrated in FIG. 2, with the solenoid-operated valve in section.

Other features may be included in addition to or alternatively to those described above to shield against external electric fields. As illustrated in FIGS. 2 and 5, in one embodiment of the invention solenoid-operated valve assemblies 58 and 60 seal openings 22 and 24 (see FIG. 1), respectively, during operation. Assemblies 58 and 60 include valve cylinders 62 and 64, respectively, that are coupled to the female-threaded ends of endpieces 18 and 20. As illustrated in FIG. 5, a male-threaded end of valve cylinder 62 is coupled to the female-threaded end of endpiece 18. A male-threaded end of a solenoid 66 is in turn coupled to a female-threaded end of valve cylinder 62 opposite its male-threaded end. A valve inlet opening 68 in valve cylinder 62 communicates fluid with sensor 10 under control of solenoid 66. Solenoid 66 includes a coil 70 and a magnetic plunger 72 arranged in the conventional manner of a solenoid. A ring 74 frictionally fit onto plunger 72 and an elastomeric bumper 76, such as an O-ring, limit the travel of plunger 72. A valve stem 78, made of a suitable conductive material, is mounted on the distal end of plunger 72. In operation, when solenoid 66 is activated by energizing coil 70, plunger 72 moves toward valve cylinder 62, urging the distal end of valve stem 78 into sealing contact with a valve seat 80 in valve cylinder 62. The distal end of valve stem 78 may be beveled or chamfered, and valve seat 80 may be correspondingly beveled or chamfered to promote sealing. When solenoid 66 is activated, valve stem 78 is not in sealing contact with valve seat 80, thereby allowing a fluid received through valve inlet 68 to flow into sensor 10. Solenoid-operated valve 64 has a structure identical to that of solenoid-operated valve 62 and is therefore not shown in similar detail.

It should be noted that valve cylinder 62 and valve stem 78 are both made of electrically conductive materials and are electrically coupled to each other as well as outer conductor 14. Thus, when solenoid 66 is activated, thereby closing solenoid-operated valve 58, no external electric field can penetrate into sensor 10.

Figure 6:
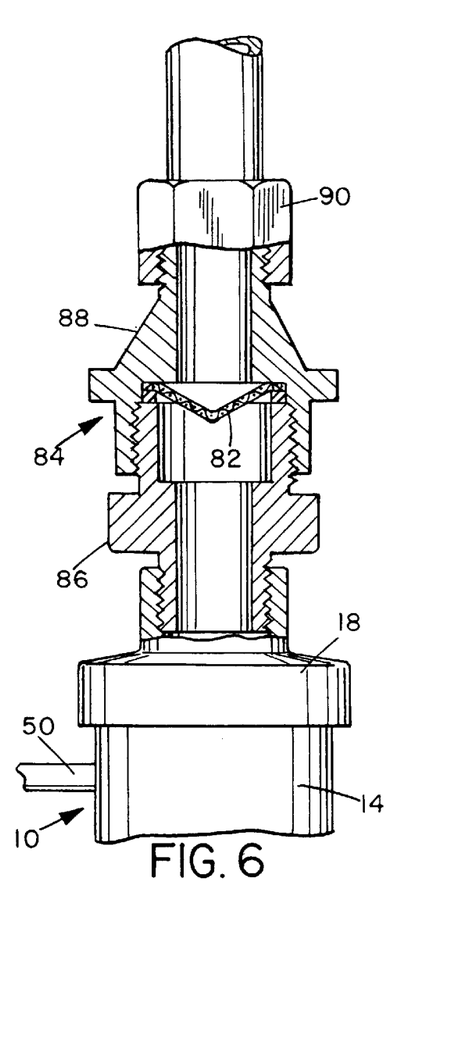
FIG. 6 is an enlargement of one end of an alternative structure having the sensor of FIG. 1 and a conductive screen assembly, with the conductive screen assembly in section.
Figure 7:
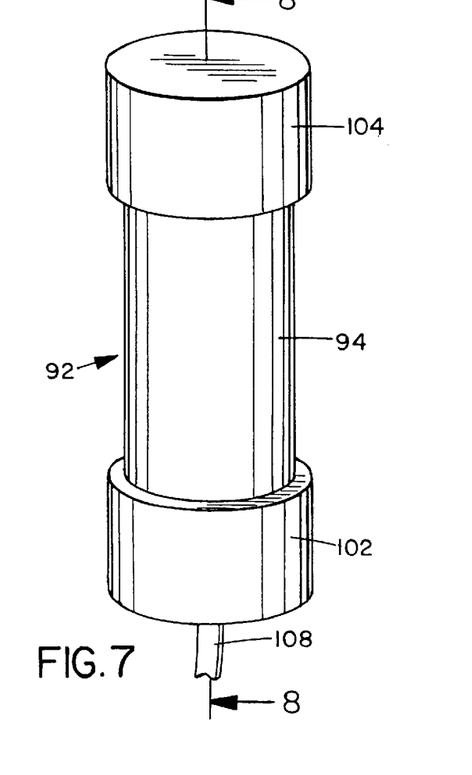
FIG. 7 is a perspective view of an alternative sensor of a type suitable for static operation.

Although FIGS. 2, 5 and 6 illustrate valve assemblies 58 and 60 oriented with respect to sensor 10 such that the outflow of fluid through outlet opening 24 is directed toward the distal end of valve stem 78, such an orientation is illustrated for purposes of convenience. If, for example, the fluid pressure is expected to be significant, it may be desirable to provide an alternative valve assembly (not shown) such that the valve stem is oriented perpendicularly to the outflow to minimize the likelihood that the pressure may force the valve open.

In an alternative embodiment, illustrated in FIG. 6, an electric field (E-field) blocking adapter 84 may be coupled to sensor 10. E-field blocking adapter 84 retains within it a screen 82 made of an electrically conductive material that shields against entry of external electric fields during operation. Screen 82 is preferably conical and has a weave that is sufficiently close to block electric fields to the extent desired, yet sufficiently coarse to permit the desired flow rate through sensor 10. Adapter 84 includes first and second adapter portions 86 and 88. A male-threaded end of first adapter portion 86 is coupled to the female-threaded end of endpiece 18. A male-threaded end of second adapter portion 88 is coupled to the female-threaded end of first adapter portion 86 at the opposite end of first adapter portion 86. Screen 82 is retained between first and second adapter portions 86 and 88. A female-threaded end of an adapter inlet 90 is coupled to a male-threaded end of second adapter portion 88. Although not shown for purposes of clarity, an identical E-field blocking adapter 84 may be coupled to endpiece 20. E-field blocking adapter 84 may be included in the invention as an alternative to solenoid-operated valve 58 or, in certain embodiments, in addition to solenoid-operated valve 58.

In other embodiments (not shown), alternative means may be used to mechanically block external E-fields. For example, a spring-loaded cap may be used in a manner similar to adapter 84. Any such means would be suitable so long as it makes electrical contact with outer conductor 14.

As illustrated in FIGS. 7–10, an alternative capacitive sensor 92 includes an elongated, generally tubular outer conductor 94 and an elongated, generally tubular inner conductor 96. A tubular insulator 98 made of glass, plastic or similar suitable material radially spaces conductors 94 and 96 from one another, thereby defining an elongated annular chamber 100. Inner conductor 96 extends into a well in the end of insulator 98 that extends into chamber 100. Insulator 98 prevents electrical conduction between conductors 94 and 96 in the presence of a fluid or other material to be measured in chamber 100. Outer conductor 94 includes two conductive endpieces 102 and 104, one at each end of sensor 92.

Endpieces 102 and 104 are female-threaded and couple to the male-threaded ends of the tubular portion of outer conductor 94. Endpiece 104 may be removed to fill chamber 100 with a fluid.

Figure 8:
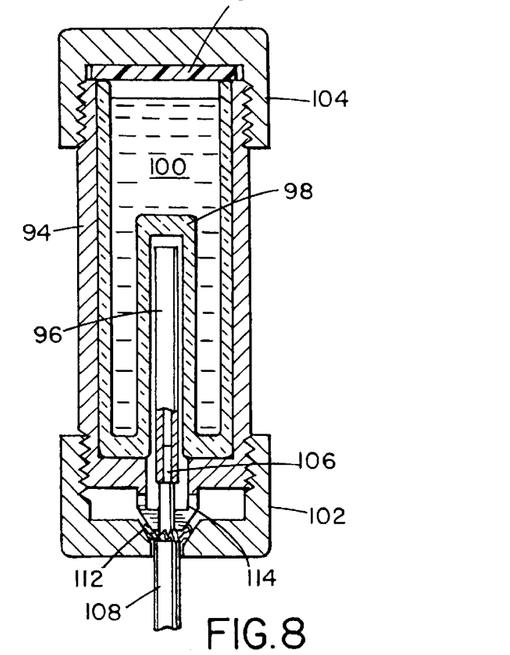
FIG. 8 is a sectional view taken on line 8—8 of FIG. 7.
Figure 9:
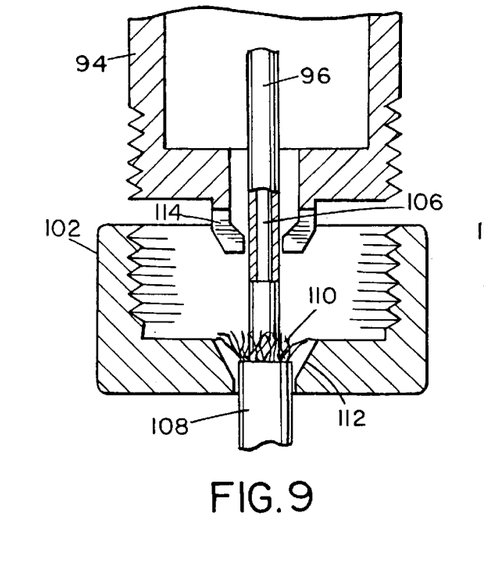
FIG. 9 is an enlarged sectional view of a portion of FIG. 8, showing the assembly of the end cap, the inner conductor, and the outer conductor.
Figure 10:
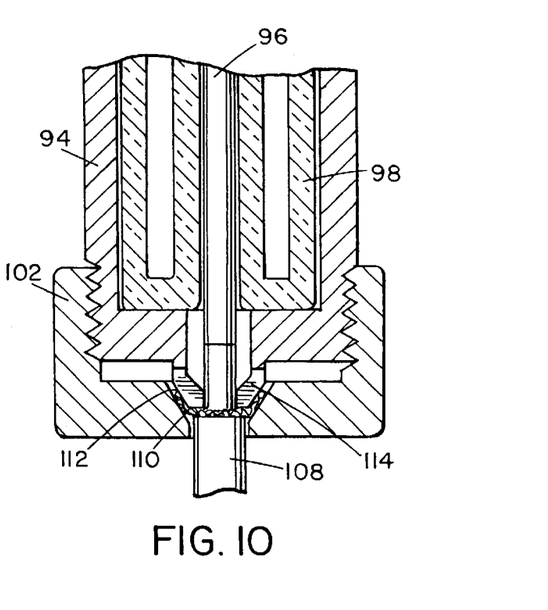
FIG. 10 is an enlarged sectional view of the assembled sensor of FIG. 8.

The central conductor 106 of a coaxial cable 108 is soldered or friction-fit inside a longitudinal bore in inner conductor 96. The shield 110 of coaxial cable 108 is retained between a frusto-conical shoulder 112 in the opening in endpiece 102 through which cable 108 extends and a correspondingly frusto-conical projection 114 in the end of the tubular portion of outer conductor 94. Because shield 110, endpiece 102, and outer conductor 94 are all electrically conductive and in contact with one another, they are all at the same ground potential and provide shielding against external electric fields.

It should be noted that with respect to each of the sensor embodiments described above, all of the electrically conductive elements are preferably made of similar metals to avoid electrolytic corrosion. Furthermore, the metals should be resistant to corrosion by the fluid with which the sensor is used. Stainless steel, copper, and brass may thus be highly suitable metals for these elements. Furthermore, an insulator (internal coating or insulating wall) may be included to protect all metal that would otherwise be in contact with fluid from a half reaction of electro-plating caused by the electric fields. As persons skilled in the art will appreciate, the nearest point allowable for metal contact with fluid depends primarily on the voltage applied to the inner plate, the distance that the metal-fluid contact point is from the inner conductor, the electrode potential of the metal, and the quantity and species of ions present in the fluid.

As more fully described below in connection with a preferred circuit, sensor 92 may be used to measure the volume charge density of a fluid. A user may unscrew endpiece 104 and fill chamber 100 with fluid. The user then replaces endpiece 104, screwing it onto the distal end of the tubular portion of outer conductor 94 to secure it. A gasket 116 between endpiece 104 and the distal end of the tubular portion of outer conductor 96 seals chamber 100 against fluid leakage. Nevertheless, when sensor 92 is filled with fluid, it is preferable to maintain it in a vertical position, as illustrated in FIG. 8. With endpieces 102 and 104 secured, chamber 100 is completely shielded against penetration of external electric fields.

Figure 11:
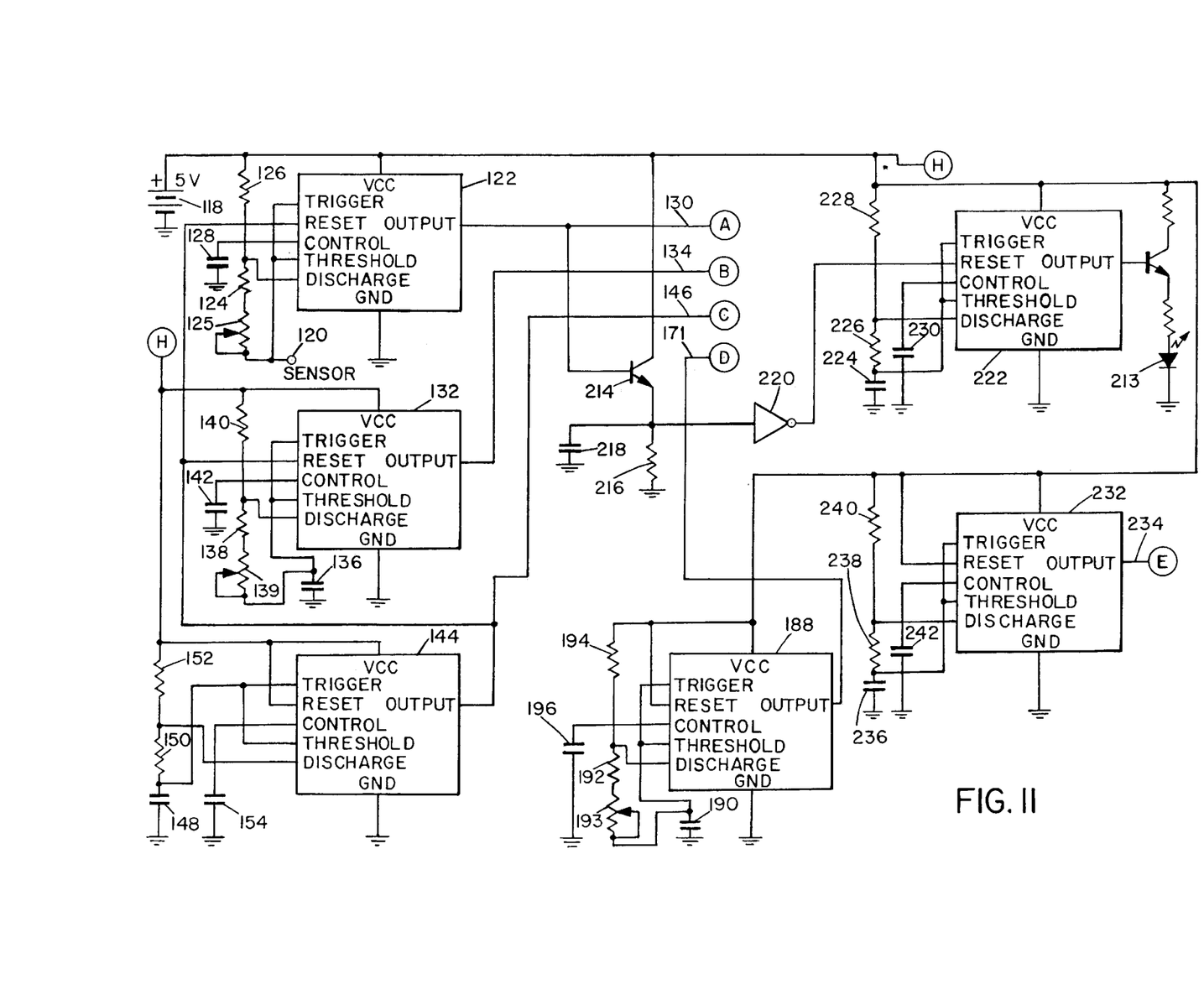
FIG. 11 is a portion of a schematic diagram illustrating a portion of a circuit for measuring volume charge density.
Figure 12:
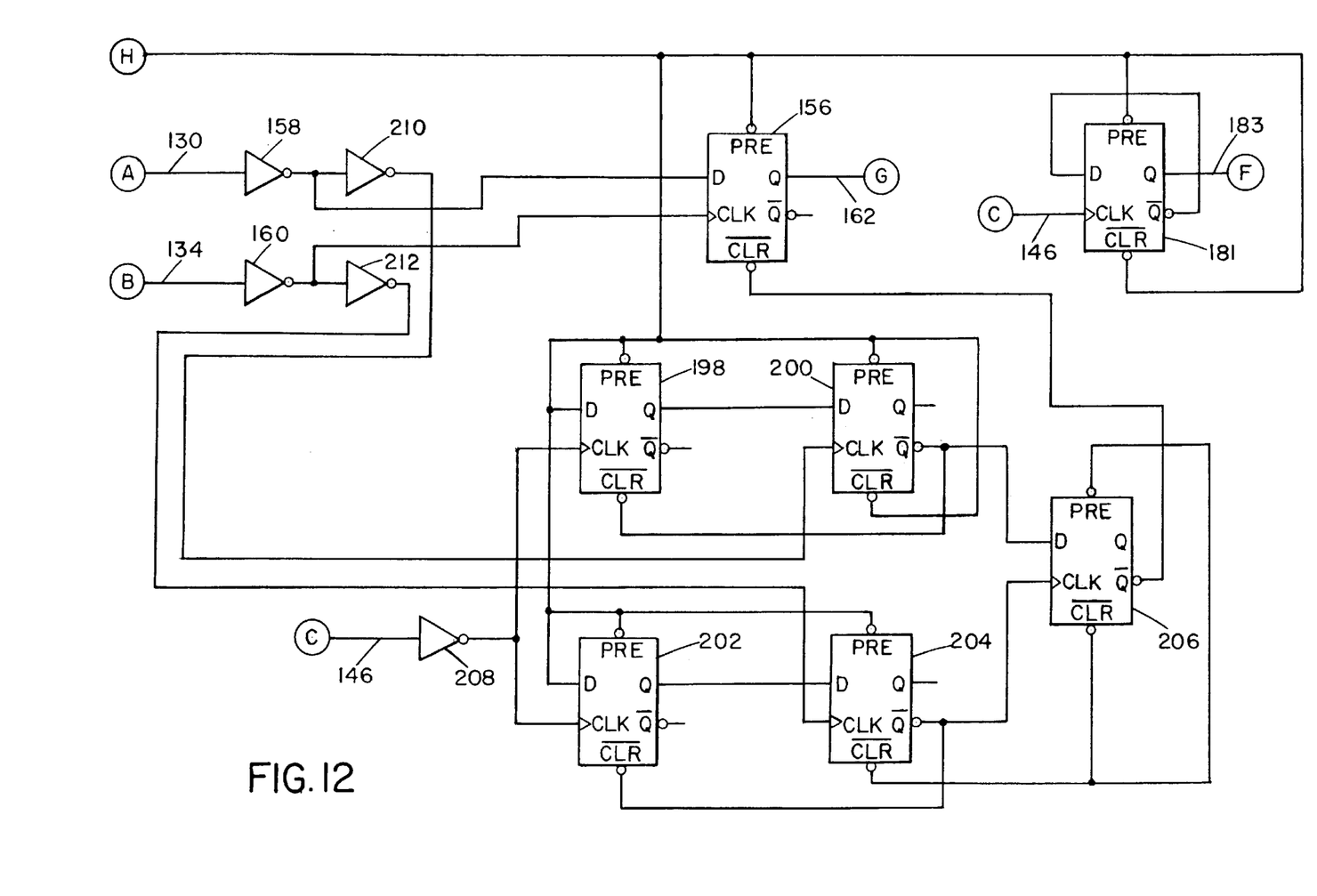
FIG. 12 is a first continuation sheet of the schematic diagram of FIG. 11 illustrating another portion of the circuit.
Figure 13:
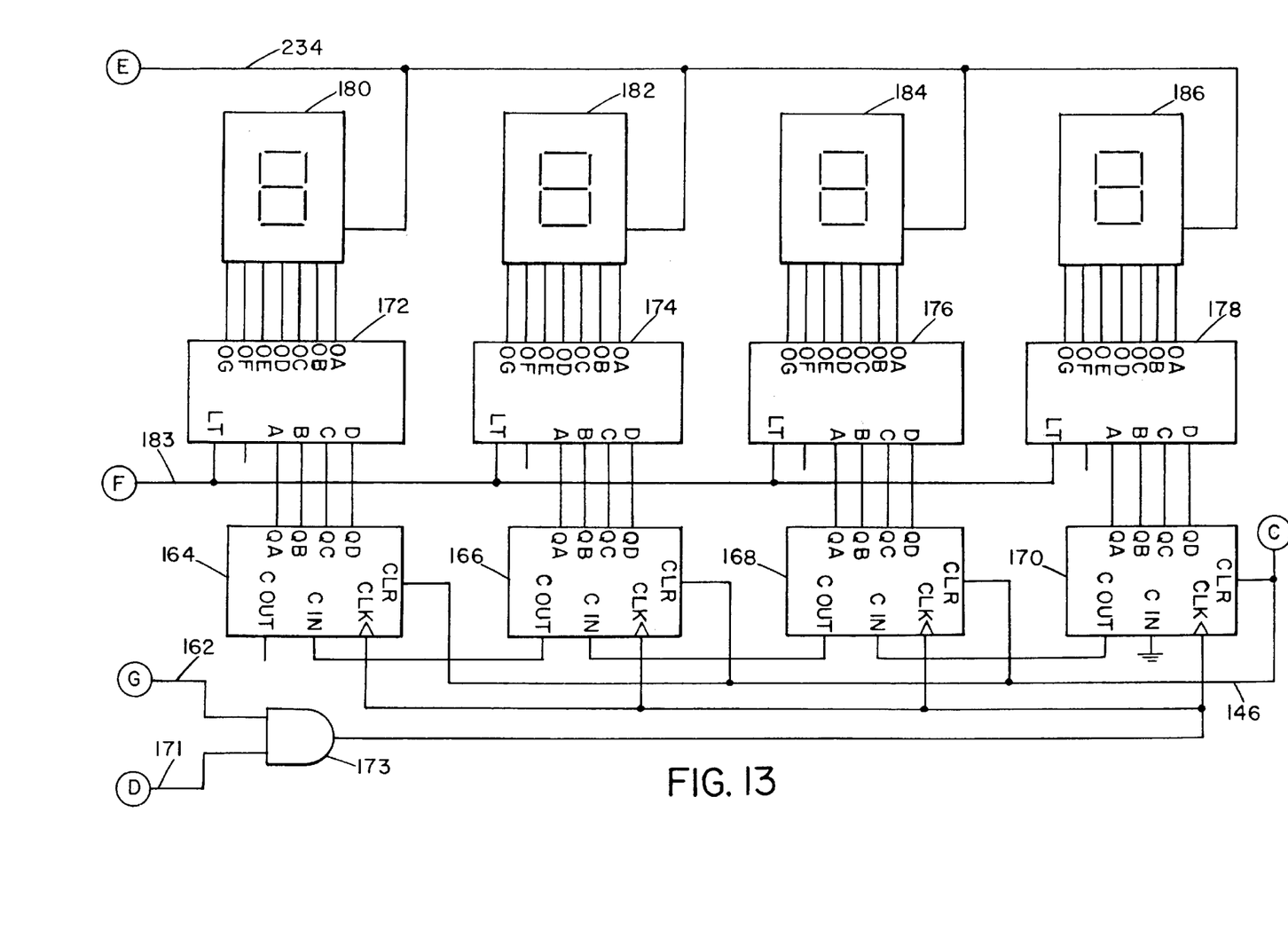
FIG. 13 is second continuation sheet of the schematic diagram of FIGS. 11–12 illustrating still another portion of the circuit.

FIGS. 11–13 illustrate a volume charge density measuring circuit that may be connected to a capacitive sensor, such as sensor 10 or sensor 92. A suitable power source, represented by a battery 118, provides a power supply voltage (+5 V) with respect to ground. The inner and outer conductors of the sensor function as the plates of a capacitor. The outer conductor of sensor 10 or 92 is grounded, as described above. The inner conductor of sensor 10 or 92 is coupled to a connector 120.

Connector 120 is coupled to the THRESHOLD and TRIGGER inputs of a 555-type timer chip 122 configured as a free-running oscillator. Two resistors 124 and 125 are connected in series with one another between connector 120 and the DISCHARGE input of timer chip 122. Resistor 125 is a variable resistor that facilitates the calibration procedure described below. Another resistor 126 is connected between the DISCHARGE input of timer chip 122 and the power supply voltage. A capacitor 128 is connected between the CONTROL input of timer chip 122 and ground. The TRIGGER and THRESHOLD inputs are connected to one another. The RESET input is connected in the manner described below. Timer chip 122 generates a test signal 130 at its output (OUTPUT) that has a frequency inversely proportional to the capacitance of the sensor to which the circuit is connected via connector 120. The R-C time constant defined by the capacitance of the sensor and the resistance of resistors 124 and 125 thus determine the frequency of test signal 130.

A second 555-type timer chip 132 configured as a free-running oscillator generates at its output (OUTPUT) a reference signal 134 that has a frequency proportional to the value of a capacitor 136, the first terminal of which is coupled to the THRESHOLD and TRIGGER inputs. The second terminal of capacitor 136 is connected to ground. Two resistors 138 and 139 are connected in series with one another between the first terminal of capacitor 136 and the DISCHARGE input of timer chip 132. Resistor 139 is a variable resistor that facilitates the calibration procedure described below. The R-C time constant defined by capacitor 136 and resistors 138 and 139 thus determine the frequency of reference signal 134. Another resistor 140 is connected between the DISCHARGE input of timer chip 132 and the power supply voltage. A capacitor 142 is connected between the CONTROL input of timer chip 132 and ground. The RESET input is connected in the manner described below.

A third 555-type timer chip 144 configured as a free-running oscillator generates at its output (OUTPUT) a trigger signal 146 that has a frequency proportional to the value of a capacitor 148, the first terminal of which is coupled to the THRESHOLD and TRIGGER inputs. The second terminal of capacitor 148 is connected to ground. A resistor 150 is connected between the first terminal of capacitor 148 and the DISCHARGE input of timer chip 144. The R-C time constant defined by capacitor 148 and resistor 150 thus determines the duty cycle of trigger signal 146. A duty cycle that produces a pulse of sufficiently short duration not to inhibit the measurement is preferred. Another resistor 152 is connected between the DISCHARGE input of timer chip 144 and the power supply voltage. A capacitor 154 is connected between the CONTROL input of timer chip 144 and ground. The RESET input is connected to the power supply voltage. Trigger signal 146 is provided to the RESET inputs of timer chips 122 and 124.

It should be noted that 555-type timers are used in these embodiments because they are economical and readily available commercially. Nevertheless, other timer circuits may be used if higher frequency operation or extreme accuracy is desired. Furthermore, the free-running oscillators described above are preferred over alternative circuits such as one-shot circuits because the capacitance values of the sensor may be small, thereby degrading the signal if one-shots are used. Conventional timer chips, such as 555 timers, are more tolerant of small capacitance values when configured to operate as free-running oscillators than when configured to operate as one-shots.

Although the operation of the circuit is described in further detail below, broadly stated, the circuit determines the frequency difference between test signal 130 and reference signal 134 by subtracting one signal from the other. Test signal 130 is coupled to the D input of a D-type monostable multivibrator or flip-flop 156 (FIG. 12), and reference signal 134 is coupled to the clock (CLK) input. Schmitt-trigger inverters 158 and 160 shape signals 130 and 134, respectively, to provide cleaner squarewaves at the D and CLK inputs of flip-flop 156. Flip-flop 156 performs the subtraction, producing at its Q output a difference signal 162 having a frequency that represents the difference between the frequencies of signals 130 and 134. A potential problem arises because difference signal 162 only accurately represents the difference frequency when test signal 130 and reference signal 134 are less than 180 degrees out-of-phase. Chip 144 synchronizes timer chips 122 and 132 by periodically resetting them simultaneously to prevent them from drifting too far out of phase. The period of trigger signal 146 should thus be greater than the periods of test signal 130 and reference signal 134, preferably several hundred or even several thousand times greater. It should be noted that the frequency of difference signal 162 is inversely proportional to the capacitance of the sensor in this embodiment.

Difference signal 162 is provided to a suitable display circuit. Although a preferred digital display circuit is illustrated in FIG. 13, any circuit that produces an indication corresponding to the measured capacitance would be suitable. In the illustrated circuit, difference signal 162 is coupled to four cascaded four-bit counter chips 164, 166, 168 and 170 via one input of a two-input AND gate 173. As described further below, a gain signal 171 is provided to the other input of AND gate 173 to facilitate calibration of the display circuit. The frequency of gain signal 171 determines the number of pulses that AND gate 173 allows to occur during each time difference slot, as described further below with regard to a calibration procedure. The output of AND gate 173 is provided to the clock (CLK) input of each of counter chips 164, 166, 168 and 170. The outputs of counter chips 164, 166, 168 and 170 are provided to four binary-coded decimal (BCD)-to-seven segment decoder/drivers 172, 174, 176 and 178, each of which in turn drives one of four single-digit seven-segment displays 180, 182, 184 and 186. A display latch signal 183 is generated by a flip-flop 181 (FIG. 12) in response to trigger signal 146 and provided to each of decoder/drivers 172, 174, 176 and 178.

The circuit may be calibrated in any suitable manner, such as that described below. Thus, displays 180, 182, 184 and 186 may display a four-digit measurement of parts-per-million or parts-per-billion of dissolved solids.

As noted above, gain signal 171 is used to calibrate the circuit. A 555-type timer chip 188 (FIG. 11) configured as a free-running oscillator produces gain signal 171, which has a frequency proportional to the value of a capacitor 190, the first terminal of which is coupled to the THRESHOLD and TRIGGER inputs. The second terminal of capacitor 190 is connected to ground. Two resistors 192 and 193 are connected in series with one another between the first terminal of capacitor 190 and the DISCHARGE input of timer chip 188. Resistor 193 is a variable resistor that facilitates the calibration procedure described below. The R-C time constant defined by capacitor 190 and resistors 192 and 193 thus determine the frequency of gain signal 171. Another resistor 194 is connected between the DISCHARGE input of timer chip 188 and the power supply voltage. A capacitor 196 is connected between the CONTROL input of timer chip 188 and ground. The RESET input is connected to the power supply voltage.

The circuit further includes a clamping circuit that clamps difference signal 162 to a zero frequency when test signal 130 has a frequency greater than that of reference signal 134. The circuit is preferably configured so that the display indicates a measurement of zero when test signal 130 has a frequency equal to that of reference signal 134. The display indicates a higher measurement when test signal 130 has a frequency lower than that of reference signal 134. The problem that the clamping circuit addresses is ensuring that the display indicates a measurement only when the sign of the frequency difference between the reference frequency and the test frequency is positive, i.e., when test signal 130 has a frequency lower than that of reference signal 134 from which it is subtracted. Absent the clamping circuit, when the frequencies of test signal 130 and reference signal 134 are close to one another, fluctuations that result in test signal 130 having a frequency higher than that of reference signal 134 would result in the display of an erroneous value.

The clamping circuit includes five D-type flip flops 198, 200, 202, 204 and 206. Flip-flops 198 and 200 are configured as a circuit often referred to as a "one-and-only-one circuit." Flip-flops 202 and 204 are also configured as a "one-and-only-one circuit." The clock (CLK) inputs of flip-flops 198 and 202 are coupled to trigger signal 146 via a Schmitt-trigger inverter 208. The D inputs of flip-flops 198 and 200 are coupled to the supply voltage. Each time trigger signal 146 is asserted, the Q outputs of flip-flops 198 and 200 produce a high signal. The Q output of flip-flop 198 is coupled to the D input of flip-flop 200. Similarly, the Q output of flip-flop 202 is coupled to the D input of flip-flop 204. The clock input of flip-flop 200 is coupled to test signal 130 via inverter 158 and another inverter 210. Similarly, the clock input of flip-flop 204 is coupled to reference signal 134 via inverter 160 and another inverter 212.

It should be noted that in other embodiments (not shown), one-and-only-one circuits may be cascaded to provide higher resolution. The resulting circuit may be referred to as, for example, a two-and-only-two or a three-and-only-three circuit.

In response to a high signal at the Q output of flip-flop 198, flip-flop 200 produces a low signal at its $\overline{Q}$ output on the next rising edge of test signal 130. Because the $\overline{Q}$ output is also coupled to the clear (CLR) input of flip-flop 198, flip-flop 198 is cleared in response to that rising edge. Thus, the output of flip-flop 200 in response to assertion of trigger signal 146 consists of exactly one cycle of test signal 130. Similarly, in response to a high signal at the $\overline{Q}$ output of flip-flop 202, flip-flop 204 produces a low signal at its $\overline{Q}$ output on the next rising edge of reference signal 134. Because the $\overline{Q}$ output is also coupled to the clear (CLR) input of flip-flop 202, flip-flop 202 is cleared in response to that rising edge. Thus, the output of flip-flop 204 in response to assertion of trigger signal 146 consists of exactly one cycle of reference signal 134.

The D input of flip-flop 206 is coupled to the $\overline{Q}$ output of flip-flop 200, and the CLK input of flip-flop 206 is coupled to the $\overline{Q}$ output of flip-flop 204. Flip-flop 206 thus compares one cycle of test signal 130 to one cycle of reference signal 146. If reference signal 134 has a frequency lower than that of test signal 130, i.e., one cycle of reference signal 134 is longer than one cycle of test signal 130, flip-flop 206 produces a low signal at its $\overline{Q}$ output. The CLR input of flip-flop 156 is coupled to the $\overline{Q}$ output of flip-flop 206. Thus, flip-flop 156 is held in a cleared state so long as reference signal 134 has a frequency lower than that of test signal 130.

The circuit further includes an error indicator circuit that produces an error indication when the frequency of test signal 130 is zero. Test signal 130 may go to zero if the circuit malfunctions or the sensor is damaged. For example, if insulator 98 of sensor 92 (FIGS. 7–10) breaks, the fluid in chamber 100 may create a conductive path between conductors 94 and 96. Test signal 130 would go to ground if a conductive path exists between conductors 94 and 96. The error detection circuit includes a light-emitting diode (LED) 213 that flashes when such a short-circuit between the inner and outer conductors of a sensor occurs.

The error indicator circuit includes a transistor 214, a resistor 216 and a capacitor 218 (FIG. 11). The collector of transistor 214 is coupled to the supply voltage; the base is coupled to test signal 130; and the emitter is coupled to one terminal of resistor 216 and one terminal of capacitor 218. The other terminals of resistor 216 and capacitor 218 are coupled to ground. Test signal 130 charges capacitor 218. Resistor 216 discharges capacitor 218 more slowly than test signal 130 charges it. Thus, the voltage on capacitor 218 remains above the value corresponding to a high logic level (typically about 2.5 volts for chips having transistor-transistor logic (TTL), although CMOS or any other chip technology would be suitable). An inverter 220 coupled to capacitor 218 produces a low output. When test signal 130 ceases to charge capacitor 218, it quickly discharges through resistor 216. When the voltage on capacitor 218 drops below the value corresponding to a low logic level (typically about 1.7 volts for TTL), inverter 220 produces a high output. The output of inverter 220 is coupled to the RESET input of a 555-type timer chip 222 that is configured as a free-running oscillator. Timer chip 222 causes LED 213 to flash. The flashing rate or cycle time is determined by the value of a capacitor 224 and a resistor 226. The first terminal of capacitor 224 is coupled to the THRESHOLD and TRIGGER inputs of timer chip 222. The second terminal of capacitor 224 is connected to ground. Resistor 226 is connected between the first terminal of capacitor 224 and the DISCHARGE input of timer chip 222. Another resistor 228 is connected between the DISCHARGE input of timer chip 222 and the power supply voltage. A capacitor 230 is connected between the CONTROL input of timer chip 222 and ground. Thus, so long as the RESET input is high, timer chip 222 produces one pulse at its output each cycle time.

The remaining circuitry relates to the display. Another 555-type timer chip 232 is configured as a free-running oscillator that produces a strobe signal 234. In response to strobe signal 234, displays 180, 182, 184 and 186 are activated at a rate determined by the value of a capacitor 236 and a resistor 238. The first terminal of capacitor 236 is coupled to the THRESHOLD and TRIGGER inputs of timer chip 232. The second terminal of capacitor 236 is connected to ground. Resistor 238 is connected between the first terminal of capacitor 236 and the DISCHARGE input of timer chip 232. Another resistor 240 is connected between the DISCHARGE input of timer chip 232 and the power supply voltage. A capacitor 242 is connected between the CONTROL input of timer chip 232 and ground.

In operation, timer chip 122, configured as a free-running test oscillator, produces test signal 130, which has a frequency inversely proportional to the capacitance of the sensor to which the circuit is coupled, such as sensor 10, sensor 92 or other suitable capacitive sensor. The capacitance is responsive to the dielectric constant or volume charge density of the fluid or other sample contained with the sensor. Timer chip 132, configured as a free-running reference oscillator, produces reference signal 134, which has an essentially constant or fixed frequency. Timer chip 144, configured as a free-running trigger oscillator, produces trigger signal 146, which periodically simultaneously resets timer chips 122 and 132 to synchronize them.

In response to test signal 130 and reference signal 134, an indicator circuit provides a user with an indication, such as a digitally displayed value, that represents the sensor capacitance. Although the indicator circuit includes a digital display in the illustrated embodiment, in other embodiments (not shown) the indicator circuit may include a binary indicator that indicates only a "Go" or "No-go" condition.

Flip-flop 156 produces difference signal 162, which has a frequency equal to the frequency difference between test signal 130 and reference signal 134. A clamping circuit, which includes two one-and-only-one circuits, ensures that flip-flop 156 responds only when the sign of difference signal 162 is positive, i.e., when test signal 130 has a frequency less than that of reference signal 134. The clamping circuit clamps difference signal 162 to zero when test signal 130 has a frequency greater than that of reference signal 134. The indicator circuit also includes cascaded counters 164, 166, 168 and 170 that produce a count in response to difference signal 162. Trigger signal 146 periodically resets the count. A digital display produces a numeric value corresponding to the count.

Figure 14:
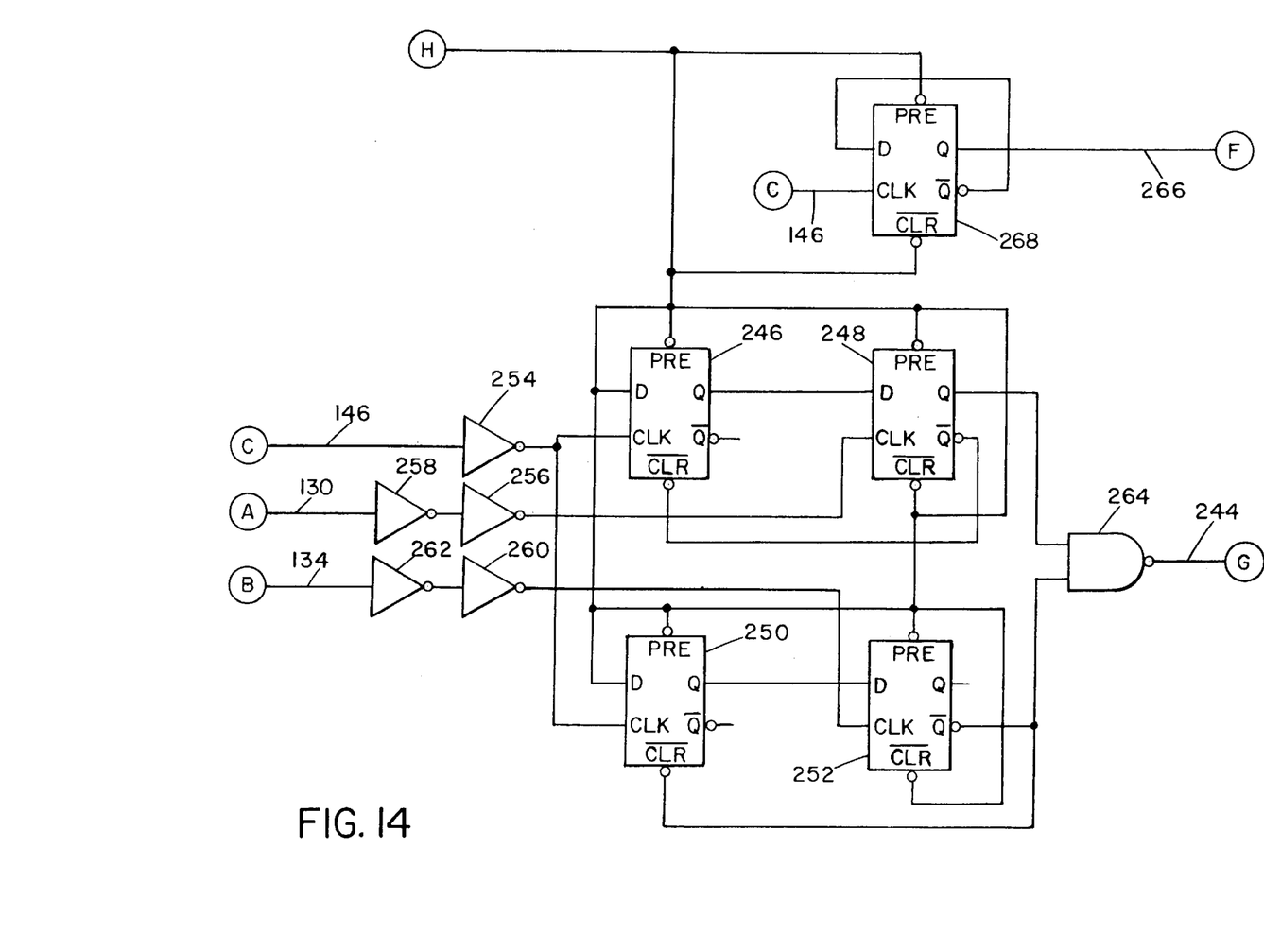
FIG. 14 is a portion of a schematic diagram illustrating an alternative portion of the circuit that may be used in place of that illustrated in FIG. 12.

FIG. 14 illustrates an alternative portion of the circuit described above that may be included in place of the portion illustrated in FIG. 12. The essence of this alternative circuit is that it provides a difference signal 244 that has a frequency directly proportional to the capacitance of the sensor, which may be desirable depending upon the type of measurements to be taken and the meaning the user assigns to the measurements. In contrast, in the embodiment described above, difference signal 162 has a frequency inversely proportional to the capacitance of the sensor.

In contrast to the circuit described above, signal 130 is coupled directly to two one-and-only-one circuits, one of which includes two D-type flip flops 246 and 248, and the other of which includes two D-type flip-flops 250 and 252. The clock (CLK) inputs of flip-flops 246 and 250 are coupled to trigger signal 146 via a Schmitt-trigger inverter 254. The D inputs of flip-flops 246 and 250 are coupled to the supply voltage. The Q output of flip-flop 246 is coupled to the D input of flip-flop 248. Similarly, the Q output of flip-flop 250 is coupled to the D input of flip-flop 252. The clock input of flip-flop 248 is coupled to test signal 130 via inverters 256 and 258. Similarly, the clock input of flip-flop 252 is coupled to reference signal 134 via inverters 260 and 262.

The Q output of flip-flop 248 is coupled to one input of an AND gate 264. The $\overline{Q}$ output of flip-flop 248 is coupled to the CLR input of flip-flop 246. The $\overline{Q}$ output of flip-flop 252 is coupled to the other input of AND gate 264 and to the CLR input of flip-flop 250. The Q output of flip-flop 252 is not connected. The output of AND gate 264 is difference signal 244.

The circuit portion illustrated in FIG. 14 generates a display latch signal 266 in the same manner as the circuit portion illustrated in FIG. 12 generates display latch signal 183. Specifically, a flip-flop 268 generates display latch signal 266 in response to trigger signal 146 and provides it to each of decoder/drivers 172, 174, 176 and 178 (FIG. 13).

A user may perform a calibration procedure prior to beginning measurement or at the time the system is manufactured. The user introduces a reference sample, such as double-distilled water, into the sensor chamber. The user then adjusts resistor 193 to increase the frequency of gain signal 171. As noted above, gain signal 171 determines the number of pulses that occur per time difference slot. The time difference slot is the interval between the clearing of the one-and-only-one circuit to which test signal 130 is coupled and the one-and-only-one circuit to which reference signal 134 is coupled. The resolution of the digital display is responsive to the number of such pulses that occur within the time difference slot. For example, if it is desired to measure between one and 2500 parts per million of impurities in a sample, the user may desire to adjust gain signal 171 such that 2500 pulses occur in the time difference slot. The user then adjusts resistor 139 until the displayed value reaches zero. The user introduces into the sensor chamber a sample of a material having the highest impurity density expected to be measured. With that sample still in the sensor chamber, the user adjusts resistor 193 until the display indicates the desired value. For example, the user may adjust resistor 193 to cause the display to indicate the volume charge density of the sample if it is known.

The measurements obtained using the present invention are more accurate than those obtained using prior measuring systems because the preferred sensor is essentially completely shielded against external electric fields during operation. In addition, the novel circuitry of the present invention is more economical than the circuitry of prior capacitive measuring systems.

Obviously, other embodiments and modifications of the present invention will occur readily to those of ordinary skill in the art in view of these teachings. Therefore, this invention is to be limited only by the following claims, which include all such other embodiments and odifications when viewed in conjunction with the above specification and accompanying drawings.

What is claimed is:

1. A capacitive sensor for testing a material sample, comprising:

an outer conductor having an elongated, substantially tubular shape with a longitudinal axis and first and second ends, and made of an electrically conductive material;

an inner conductor having an elongated, substantially tubular shape with a longitudinal axis and first and second ends, and made of an electrically conductive material;

a chamber electrically insulated from said inner and outer conductors having an elongated, substantially tubular shape with a longitudinal axis and first and second ends, said chamber disposed between said inner and outer conductors and coaxially aligned with said inner and outer conductors;

said outer conductor having an opening in communication with said chamber, said outer conductor defining a shield against penetration by an electric field, said shield completely enclosing said chamber but for said opening in said outer conductor; and a valve attached to said opening and having a movable sealing member made of conductive material electrically coupled to said outer conductor, said sealing member selectably movable to open and close said opening.

2. The capacitive sensor recited in claim 1, wherein said valve is solenoid-operated.

3. The capacitive sensor recited in claim 2, wherein:

said outer conductor includes a first opening at said first end of said outer conductor and a second opening at said second end of said outer conductor;

said capacitive sensor includes a first solenoid-operated valve attached to said first opening and having a movable sealing member made of conductive material electrically coupled to said outer conductor, said sealing member selectably movable to open and close said first opening; and said capacitive sensor includes a second solenoid-operated valve attached to said second opening and having a movable sealing member made of conductive material electrically coupled to said outer conductor, said sealing member selectably movable to open and close said second opening.

4. The capacitive sensor recited in claim 1, wherein:

said chamber is defined by a tubular insulator having a closed first end and an open second end, with an electrically insulated well extending into said chamber at said first end of said tubular insulator for receiving said inner conductor;

said open end of said tubular insulator is at said first end of said outer conductor; and said opening of said outer conductor is at said first end of said outer conductor.

5. The capacitive sensor recited in claim 4, wherein said sealing member comprises a cap threadably connectable to said outer conductor.

6. The capacitive sensor recited in claim 1, further comprising:

a test oscillator circuit coupled to said inner conductor for producing a test signal having a test frequency;

a reference oscillator circuit for producing a reference signal having a reference frequency; and an indicator circuit for producing a measurement signal in response to said test frequency and said reference frequency and for displaying a representation of said measurement signal.

7. The capacitive sensor recited in claim 6, wherein said indicator circuit comprises:

a D-type flip-flop having a clock input and a D input, said clock input receiving one of said test signal and said reference signal, and said D input receiving the other of said test signal and said reference signal; and a display for displaying a measurement indication in response to an output of said flip-flop.

8. The capacitive sensor recited in claim 7, further comprising a trigger oscillator for producing a synchronizing signal, said synchronizing signal periodically simultaneously resetting said test oscillator and said reference oscillator.

9. The capacitive sensor recited in claim 8, further comprising a clamping circuit for clamping said representation of said measurement signal to a predetermined value when a difference between said test frequency and said reference frequency has a predetermined sign.

10. The capacitive sensor recited in claim 6, further comprising an error indicator circuit for producing an error indication when said frequency of said test signal is zero.

11. A capacitive sensor for testing a material sample, comprising:

an outer conductor having an elongated, substantially tubular shape with a longitudinal axis and first and second ends, and made of an electrically conductive material;

an inner conductor having an elongated, substantially tubular shape with a longitudinal axis and first and second ends, and made of an electrically conductive material;

a chamber electrically insulated from said inner and outer conductors having an elongated, substantially tubular shape with a longitudinal axis and first and second ends, said chamber disposed between said inner and outer conductors and coaxially aligned with said inner and outer conductors;

said outer conductor having an opening in communication with said chamber, said outer conductor defining a shield against penetration by an electric field, said shield completely enclosing said chamber but for said opening in said outer conductor; and a screen made of a conductive material, said screen having a porous mesh structure and disposed in said opening and electrically coupled to said outer conductor.

12. The capacitive sensor recited in claim 11, wherein:

said outer conductor includes a first opening at said first end of said outer conductor and a second opening at said second end of said outer conductor;

said capacitive sensor includes a first screen made of an electrically conductive material, said first screen disposed in said first opening and electrically coupled to outer conductor; and said capacitive sensor includes a second screen made of an electrically conductive material, said second screen disposed in said second opening and electrically coupled to outer conductor.

13. The capacitive sensor recited in claim 11, wherein said chamber is defined by dielectric coatings on an inner surface of said outer conductor and on an outer surface of said inner conductor.

14. The capacitive sensor recited in claim 11, further comprising:

a test oscillator circuit coupled to said inner conductor for producing a test signal having a test frequency;

a reference oscillator circuit for producing a reference signal having a predetermined reference frequency; and an indicator circuit for producing a measurement signal in response to said test frequency and said reference frequency and for displaying a representation of said measurement signal.

15. The capacitive sensor recited in claim 14, wherein said indicator circuit comprises:

a D-type flip-flop having a clock input and a D input, said clock input receiving one of said test signal and said reference signal, and said D input receiving the other of said test signal and said reference signal; and a display for displaying a measurement indication in response to an output of said flip-flop.

16. The capacitive sensor recited in claim 15, further comprising a trigger oscillator for producing a synchronizing signal, said synchronizing signal periodically simultaneously resetting said test oscillator and said reference oscillator.

17. The capacitive sensor recited in claim 15, further comprising a clamping circuit for clamping said indication to a predetermined value when a difference between said test frequency and said reference frequency has a predetermined sign.

18. The capacitive sensor recited in claim 15, further comprising an error indicator circuit for producing an error indication when said frequency of said test signal is zero.

* * * * *